United States Patent
Akimoto et al.

(10) Patent No.: US 9,782,377 B2
(45) Date of Patent: Oct. 10, 2017

(54) COMPOSITION FOR NORMALIZATION OF INFRADIAN RHYTHM

(75) Inventors: Kengo Akimoto, Kawasaki (JP); Yoshiko Ono, Osaka (JP); Hiroshi Kawashima, Takatsuki (JP); Katsuya Nagai, Minoo (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 1155 days.

(21) Appl. No.: 10/546,158

(22) PCT Filed: Mar. 26, 2004

(86) PCT No.: PCT/JP2004/004318
§ 371 (c)(1),
(2), (4) Date: Aug. 22, 2005

(87) PCT Pub. No.: WO2004/084882
PCT Pub. Date: Oct. 7, 2004

(65) Prior Publication Data
US 2006/0073187 A1    Apr. 6, 2006

(30) Foreign Application Priority Data
Mar. 27, 2003 (JP) .................. 2003-088956

(51) Int. Cl.
*A61K 31/202* (2006.01)
*A23L 1/30* (2006.01)
*A23L 33/12* (2016.01)

(52) U.S. Cl.
CPC ............ *A61K 31/202* (2013.01); *A23L 33/12* (2016.08)

(58) Field of Classification Search
CPC ..................... A23L 1/3008; A61K 31/202
See application file for complete search history.

(56) References Cited

U.S. PATENT DOCUMENTS

| | | | |
|---|---|---|---|
| 5,242,941 A * | 9/1993 | Lewy et al. | 514/416 |
| 6,069,138 A * | 5/2000 | Ponroy | 514/77 |
| 6,184,251 B1 | 2/2001 | Stordy et al. | |
| 2004/0266874 A1 * | 12/2004 | Akimoto et al. | 514/560 |

FOREIGN PATENT DOCUMENTS

| | | |
|---|---|---|
| EP | 0 920 323 A1 | 6/1999 |
| EP | 1 283 038 A1 | 2/2003 |
| EP | 1 283 038 A1 | 12/2003 |
| EP | 1419768 | 5/2004 |
| JP | 6-505384 | 6/1994 |
| JP | 2003048831 | 2/2003 |
| WO | WO 92/13086 | 8/1992 |
| WO | 96/21037 | 7/1996 |
| WO | WO 96/21037 | 7/1996 |
| WO | WO 98/50052 | 11/1998 |
| WO | 03/013497 A1 | 2/2003 |
| WO | 2004/028529 A1 | 4/2004 |

OTHER PUBLICATIONS

Nir, I. Melatonin for the Treatment of Disorders in Circadian Rhythm and Sleep: Could it Form a Basis for Medication? Receptors and Channels, 9: 379-385, 2003.*
Database WPI Section Ch, Week 200324, Derwent Publications Ltd., London GB, AN 2003-248234, XP002293445 Abstract of WP 2003/013497 (Feb. 2003).
International Search Report issued Sep. 2, 2004, in International Application No. PCT/JP2004/004318 filed Mar. 26, 2004.
Vaneček et al., "Melatonin modulates diacylglycerol and arachidonic acid metabolism in the anterior pituitary of immature rats," Neuroscience Letters, 1990, vol. 110, pp. 199-203.
Korean Office Action issued Mar. 10, 2011, in Korean Application No. 7017769/2005 (with English language translation).
S. P. James et al., "Melatonin Administration in Insomnia," Neuropsychopharmacology, vol. 3, No. 1, Feb. 1990, pp. 19-23.
I. V. Zhdanova et al., "Sleep-inducing effects of low doses of melatonin ingested in the evening," Pharmacodynamics and Drug Action, Clinical Pharmacology & Therapeutics, vol. 57, No. 5, pp. 552-558.
A. Herxheimer, et al., "Melatonin for the prevention and treatment of jet lag," *Cochrane Database Syst. Rev.* 2: CD001520 (2002); obtainable at: <https://www.ncbi.nlm.nih.gov/pubmed/12076414>.
Simon P. Fisher, et al., "Acute sleep-promoting action of the melatonin agonist, ramelteon, in the rat," *J. Pineal Res.* 45: 125-132 (2008).
Folch, et al., "A Simple Method for the Isolation and Purification of Total Lipids From Animal Tissues", J. Biol.Chem., 1957, 226, 497-509.

* cited by examiner

Primary Examiner — Sreeni Padmanabhan
Assistant Examiner — Jody Karol
(74) Attorney, Agent, or Firm — Drinker Biddle & Reath LLP

(57) ABSTRACT

A composition having a normalizing action for infradian rhythm and/or a synchronization promoting action for circadian rhythm (biological clock) containing arachidonic acid and/or an arachidonic acid-containing compound.

26 Claims, 3 Drawing Sheets

Fig. 2
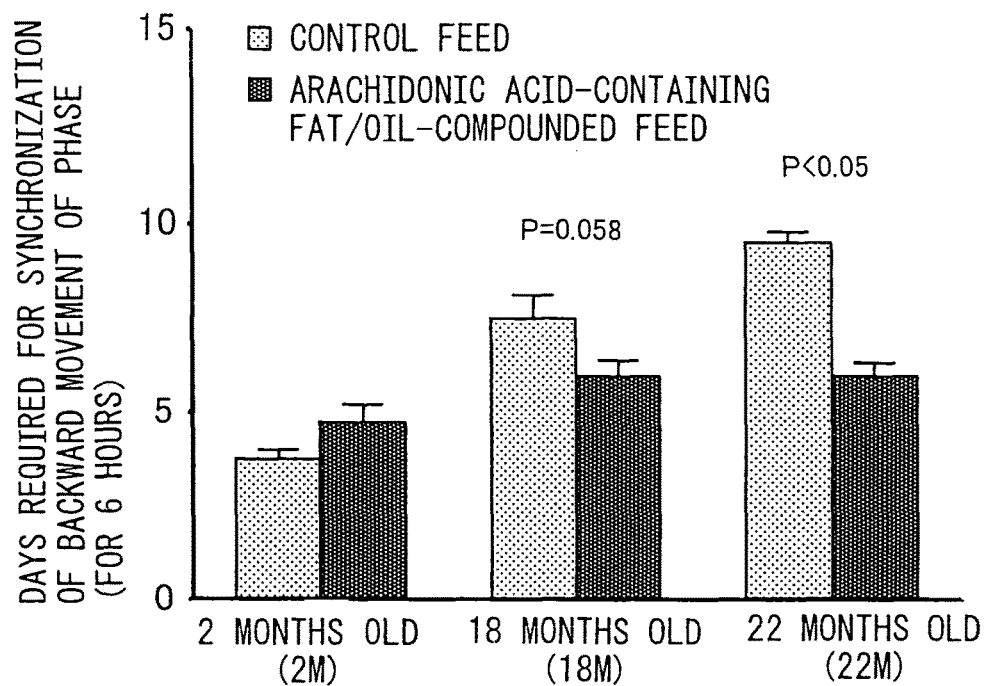
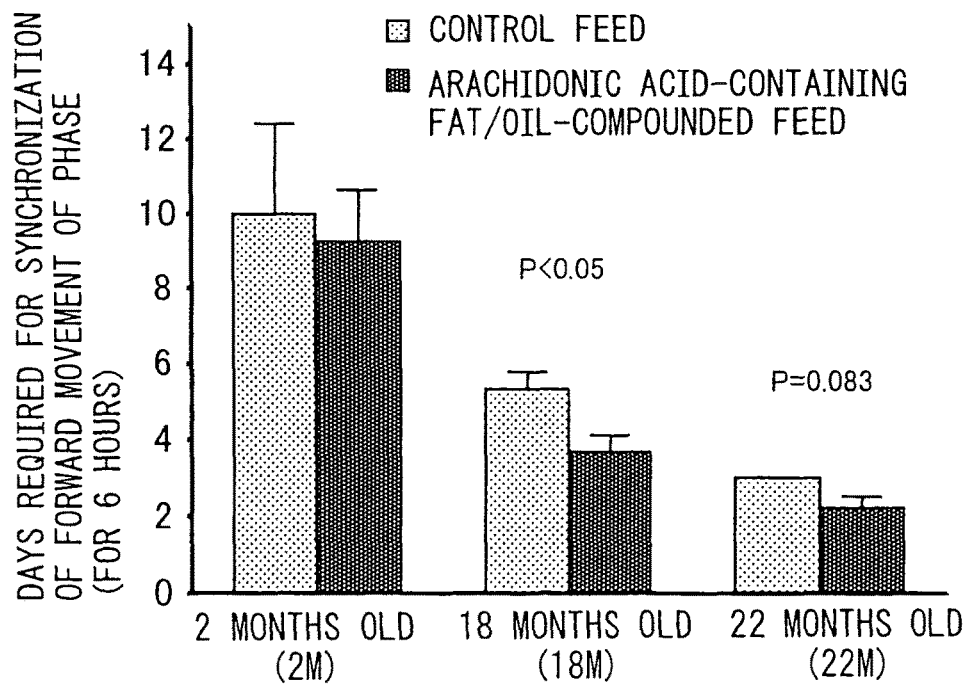

Fig. 3
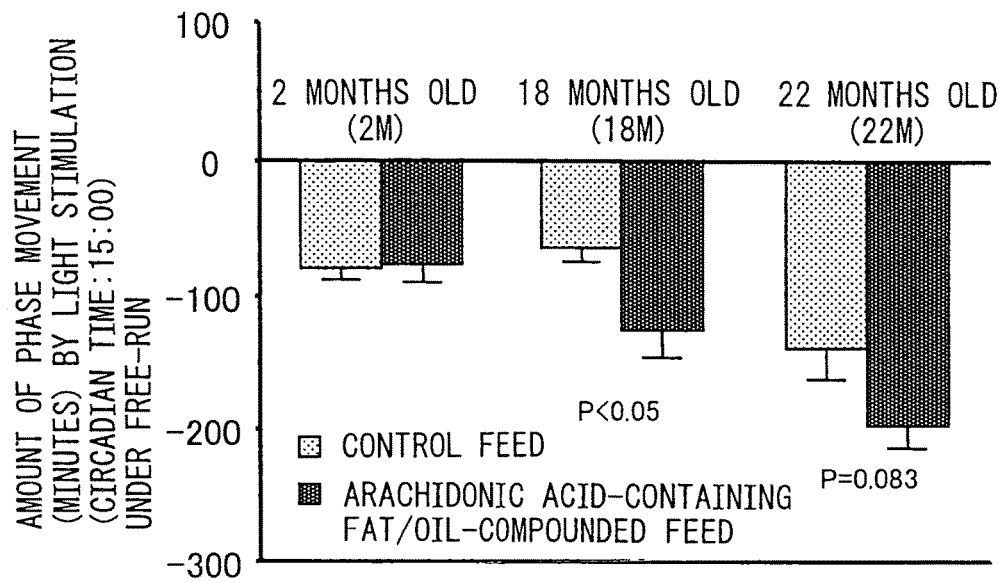
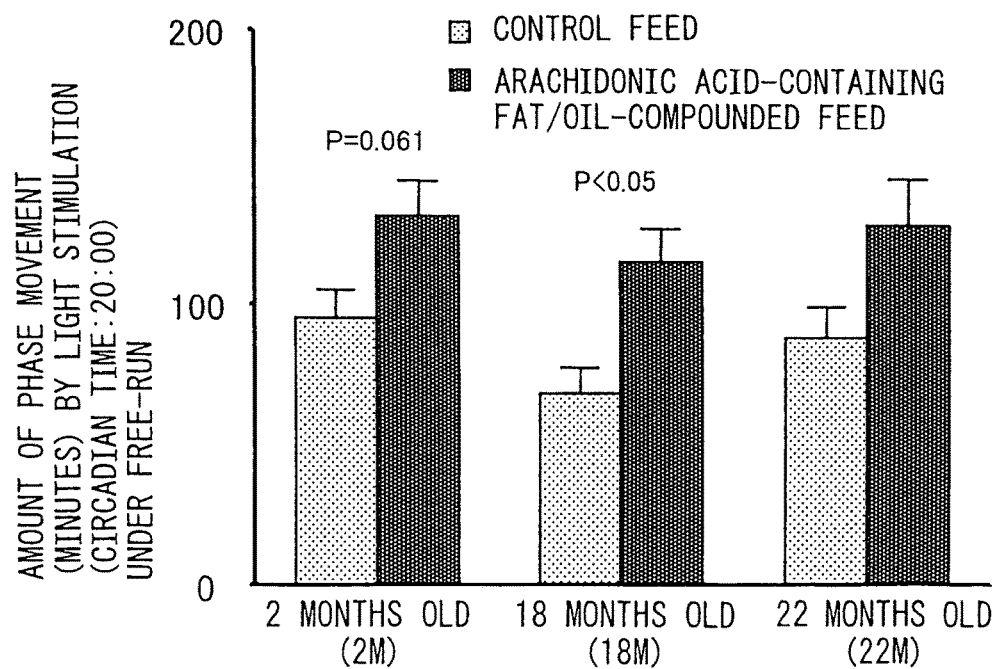

COMPOSITION FOR NORMALIZATION OF INFRADIAN RHYTHM

TECHNICAL FIELD

The present invention provides a composition concerning adjustment of circadian rhythm.

BACKGROUND ART

Various functions of human beings and other organisms grow within a limited range and the variation thereof has a regular periodicity. This is called biorhythms in general. The most fundamental biorhythm is a variation having a cycle of approximately one day and is called a circadian rhythm. The circadian rhythm is an endogenous rhythm operated by "program which counts the time autonomously" inherent to the living body itself, or the so-called endogenous clock function (which is also called a biological clock or body clock) and is different from an exogenous rhythm which is entirely dependent upon physical changes surrounding the living body (such as day and night, rotation of the earth, and changes in temperature, humidity and atmospheric pressure).

These rhythms can be discriminated by checking whether the rhythm still exists when outside factors are removed as completely as possible. In an environment where periodicity has no effect, such as in a laboratory which is isolated from the outside, the human body exhibits a cycle of longer than 24 hours. Such a cycle is called a free-run cycle and is believed to be an endogenous cycle, or body clock (the free-run cycle of a human being is 24.2 hours).

A body clock with a free-run cycle that is not 24 hours, synchronizes with outside physical changes, and usually agrees with the changes in day and night, to give a 24-hour cycle. This is called rhythm synchronization and the resulting rhythm in 24-hour cycles is called infradian rhythm. However, synchronization of rhythm means not only a mere agreement of 24 hour cycles but also an establishment of a time relation of 1:1 between the specific phase of the body clock and that of the exogenous environmental rhythm, the latter being more important. For example, the initiation time of activity periods of animals is determined by the body clock. In diurnal animals, as a result of rhythm synchronization, there is an agreement between sunrise which is a specific phase of the environmental rhythm and activity periods which are established by specific phases of the body clock.

Infradian rhythm appears not only in sleep habits and diet, but also in body temperature, blood pressure, heart rate and internal secretion, and in the treatment and prevention of diseases of the heart and blood vessel systems, it is believed to be important to understand the infradian rhythms of the autonomic nervous system, endocrine system, hemodynamics, etc. and to maintain them normally. In modern society where artificial and irregular life cycles are imposed by shift work, travel by air over long distances, aging society, diversification of life styles, etc. is becoming usual, there has been an unexpected increase in various diseases caused by biorhythm disorders, such as infradian rhythm sleep disorder and there has been a brisk demand for an effective countermeasure for treating these diseases.

In an asynchronous syndrome (jet lag) due to abnormality of infradian rhythm, insomnia at night or sleeping in the daytime may result, moreover, headache, tinnitus, palpitation, nausea, gastralgia and diarrhea may also result, causing a decrease in judgment and concentration. In addition, delayed sleep phase syndrome (DSPS) is the highest at the onset of puberty (Diagnostic Classification Steering Committee, Thorpy, M. J.: International Classification of Sleep Disorders: Diagnostic and Coding Manual. American Sleep Disorders Association, Rochester, 1990). An infradian rhythm sleep disorder in young people makes their adaptation to society difficult and their development is inhibited (Kajimura, N., et al.: *Nippon Rinsho*, Vol. 56, No. 2, page 404, 1998).

As a method for adjusting the abnormality of infradian rhythm causing such symptoms, there are a psychotherapeutic approach, non-drug therapy and drug therapy. As a non-drug therapy, irradiation with bright light is available, and at present, it is positively used for the treatment of seasonal emotional disorder and infradian rhythm sleep disorder. Hypnotics which are used for drug therapy are roughly classified as barbiturate type, non-barbiturate type and benzodian type. Although the drugs of a barbiturate type have a strong sleep-inducing action, they are also toxic, and their tendency to suppress respiration and circulation becomes stronger as the concentration thereof in the blood is increased, so that their use must be carefully controlled.

In the drugs of a non-barbiturate type, suppressed respiration, vomiting, nausea and coma can result, and there is a risk of dependency. Therefore, at present, drugs of a benzodian type are in the mainstream in view of safety, but side effects such as antianxiety action, anticonvulsant action and muscle relaxing action are believed to be expressed. It has been also known that "hangover effect" and "amnesia effect" in which sleepiness, swaying, dizziness, fatigue and lassitude remain are strongly expressed, and thus the use of these drugs must be very carefully controlled. Thus, so far there is no excellent compound having a safe and effective normalizing action for infradian rhythm. Furthermore, hypnotics merely induce sleep and have no action of synchronizing to circadian rhythm. For example, when synchronizing to circadian rhythm, it is possible to relieve jet lag, but hypnotics are unable to do that.

As a compound which is able to synchronize to the circadian rhythm, melatonin has been suggested. Melatonin is a hormone which is mostly produced by the pineal gland and its production exhibits a significant change throughout the day. Production at night is as high as 50- to 100-fold that in the daytime.

When the production of melatonin at night is suppressed by administration of a β-blocker, sleeping-waking rhythm disorders, such as deterioration of sleeping, e.g. increase in intermediate awaking at night (Brismar, et al.: *Acta Med. Scand.*, 223, p. 525, 1988) and lowering of awaking level in daytime (Dimenas, et al.: *J. Clin. Pharmacol.*, 30, s103, 1990) may result. As there is a decrease in the secretion of melatonin in older people, supplementing melatonin has been said to be an effective remedy (Garfinkel, et al.: *Lancet*, 346, p. 541, 1995). Even in very old people where physiological production of melatonin decreases significantly, the amount of melatonin produced is still high in those who are able to have good sleep (Haimov, et al.: *Sleep*, 18, p. 598, 1995). From these facts, it has been believed that endogenous melatonin is a physiological hypnotic substance participating in adjustment of sleeping-waking rhythm.

There have been many reports on the hypnotic action of endogenous melatonin for the purpose of synchronization of circadian rhythm. However, although there is a report that, as a result of administration of melatonin, good quality sleep, such as shortening of hypnagogic latency time, decrease in midway awaking and improvement of insomnia can be achieved (Zhdanova, et al.: *Clin. Pharmacol. Ther.*, 57, p. 552, 1995), there is also another report that adjusting effect of sleeping and improving affect for sleep disorder are denied (James, et al.: *Neuropsychopharmacology*, 3, p. 19, 1990).

Non-Patent Document 1

Brismar, et al.: *Acta Med. Scand.*, 223, p. 525, 1988

Non-Patent Document 2

Dimenas, et al.: *J. Clin. Pharmacol.*, 30, s103, 1990

Non-Patent Document 3

Garfinkel, et al.: *Lancet*, 346, p. 541, 1995

Non-Patent Document 4

Haimov, et al.: *Sleep*, 18, p. 598, 1995

Non-Patent Document 5

Zhdanova, et al.: *Clin. Pharmacol. Ther.*, 57, p. 552, 1995

Non-Patent Document 6

James, et al.: *Neuropsuchopharmacology*, 3, p. 19, 1990

BRIEF EXPLANATION OF THE DRAWINGS

FIG. 2 shows the influence of the arachidonic acid-containing fat/oil on the circadian rhythm synchronization accompanied by backward and forward movements of a 6-hour phase.

FIG. 3 shows the influence of the arachidonic acid-containing fat/oil on the amount of movement of phase (time) to backward movement of the phase and forward movement of the phase by light stimulation to rats upon feeding (free-run) under the dark condition for 24 hours.

DISCLOSURE OF THE INVENTION

Figure 1:
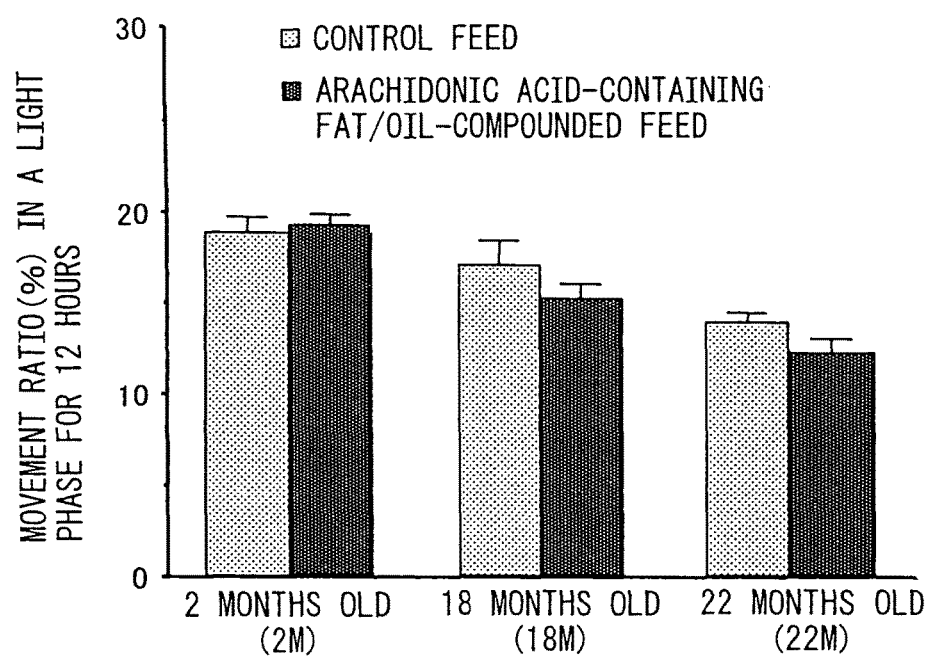
FIG. 1 shows the influence of the arachidonic acid-containing fat/oil on the movement rate (%) in a light period for 12 hours.

It is pointed out (Mishima: *Nippon Rinsho*, Vol. 56, No. 2, p. 302, 1998) that one of the reasons why those results contrary to each other are obtained resides in, dependency on the administered time and there has not been known any compound at all which is not dependent upon the administering time and has normalizing action for infradian rhythm and/or promoting action for synchronization of circadian rhythm (biological clock).

Therefore, there has been a strong demand for developing a compound which promotes the normalizing action for infradian rhythm and/or the synchronization of circadian rhythm (biological clock), has little side effect and is excellent in application to drugs and foods.

Accordingly, the present invention is aimed to provide a food/beverage having a normalizing action of infradian rhythm and/or a synchronization promoting action for circadian rhythm (biological clock), containing arachidonic acid and/or an arachidonic acid-containing compound, and also to provide a method for manufacturing the same. More particularly, the object of the present invention is to provide a food/beverage having an improving action to biorhythm disorder, sleep disorder and delayed sleep phase syndrome caused by abnormality of infradian rhythm and also to disorder caused by retardation of synchronization of circadian rhythm (biological clock) (such as jet lag, headache, tinnitus, palpitation, nausea, gastralgia, diarrhea and lowering in ability of judgment and concentration) where at least one member selected from arachidonic acid, alcohol ester of arachidonic acid and triglyceride, phospholipid and glycolipid in which a part of or all of the constituting fatty acid is arachidonic acid is an effective ingredient and also to provide a method for manufacturing the same.

The present inventors have carried out intensive studies with a purpose of clarifying a normalizing action for infradian rhythm and/or a synchronization promoting action of circadian rhythm (biological clock) of arachidonic acid and/or an arachidonic acid-containing compound. The effect of arachidonic acid and/or an arachidonic acid-containing compound has been clarified behavior-pharmacologically by evaluation of the effect on synchronization of circadian rhythm of rat.

The present inventors have further succeeded in an industrial production of a triglyceride containing not less than 10% by weight of arachidonic acid using a microorganism whereupon it is now possible to subject it to a test for the effect of the present invention and the effect of the said triglyceride has been clarified.

The present inventors have furthermore succeeded in the manufacture of fat/oil containing triglycerides where medium-chain fatty acids are bonded to 1,3-positions and arachidonic acid is bonded to 2-position by an enzymatic method whereupon it is now possible to subject it to a test for the effect of the present invention and the effect of the said triglyceride has been clarified.

Accordingly, the present invention is aimed to provide a beverage/food having a normalizing action for infradian rhythm and/or a synchronization promoting action for circadian rhythm (biological clock), containing arachidonic acid and/or an arachidonic acid-containing compound as an effective ingredient, and also to provide a method for manufacturing the same.

More particularly, the present invention provides a food/beverage having an alleviating action to biorhythm disorder, sleep disorder and delayed sleep phase syndrome caused by abnormality of infradian rhythm and also to disorder caused by retardation of synchronization of circadian rhythm (biological clock) (such as jet lag, headache, tinnitus, palpitation, nausea, gastralgia, diarrhea and lowering in ability of judgment and concentration) where at least one member selected from arachidonic acid, alcohol ester of arachidonic acid and triglyceride, phospholipid and glycolipid in which a part of or all of the constituting fatty acid is arachidonic acid is an effective ingredient and also to provide a method for manufacturing the same.

In accordance with the present invention, it is possible to provide a food/beverage having a normalizing action of infradian rhythm and/or a synchronization promoting action for circadian rhythm (biological clock), containing arachidonic acid and/or an arachidonic acid-containing compound, and also to provide a method for manufacturing the same and that is particularly useful for humans in the modern society.

Accordingly, the present invention provides (1) a composition having a normalizing action of infradian rhythm and/or a synchronization promoting action for circadian rhythm (biological clock), containing arachidonic acid and/or an arachidonic acid-containing compound. The above-mentioned arachidonic acid-containing compound is preferably an alcohol ester of arachidonic acid, or triglyceride, phospholipid or glycolipid comprising arachidonic acid as a part of or all of the constituting fatty acid. The triglyceride comprising arachidonic acid as all of or a part of the constituting fatty acids is preferably a triglyceride where a medium-chain fatty acids are bonded to 1,3-positions and arachidonic acid is bonded to 2-position. The above-mentioned medium-chain fatty acid is preferably selected from fatty acids having 6 to 12 carbons and, for example, selected from fatty acids having 8 carbons.

The present invention also provides (2) a composition having a normalizing action of infradian rhythm and/or a synchronization promoting action for circadian rhythm (biological clock), containing triglycerides comprising a triglyceride comprising arachidonic acid as all of or a part of a constituting fatty acid. The ratio of arachidonic acid of the triglycerides comprising a triglyceride comprising arachidonic acid as all of or a part of the constituting fatty acid is preferably not less than 10% by weight to total fatty acids which constitute the triglyceride. The triglycerides comprising a triglyceride comprising arachidonic acid as all of or a part of the constituting fatty acid is preferably extracted from a microorganism belonging to genus *Mortierella*. The triglycerides comprising a triglyceride comprising arachidonic acid as all of or a part of the constituting fatty acid is preferably a triglyceride which does not contain eicosapentaenoic acid or, even if contained, its amount is not more than 1%.

The present invention further provides a composition having a normalizing action of infradian rhythm and/or a synchronization promoting action for circadian rhythm (biological clock), containing triglycerides which contain not less than 5 mol % of a triglyceride where a medium-chain fatty acids are bonded to 1,3-positions and arachidonic acid is bonded to 2-position. The above-mentioned medium-chain fatty acid is preferably selected from fatty acids having 6 to 12 carbons and, for example, selected from fatty acids having 8 carbons.

The composition mentioned in the above (1) to (3) preferably has a preventive or alleviating action for biorhythm disorder caused by abnormality of infradian rhythm. Examples of the biorhythm disorder are sleep disorder, disorder by retardation of synchronization of circadian rhythm (biological clock) as well as jet lag, headache, tinnitus, palpitation, nausea, gastralgia, diarrhea and lowering in ability of judgment and concentration caused by retardation of synchronization of circadian rhythm (biological clock).

Examples of an embodiment of the above-mentioned composition (1) to (3) are a food composition and a pharmaceutical composition. The ingesting amount for an adult per day is preferably 0.001 to 20 g in terms of the amount of arachidonic acid. The compound where arachidonic acid is a constituting fatty acid is preferably an alcohol ester of arachidonic acid or triglyceride, phospholipid or glycolipid in which a part of or all of the constituting fatty acid is arachidonic acid. The above-mentioned triglyceride in which all of or a part of the constituting fatty acid is arachidonic acid is a triglyceride where medium-chain fatty acids are bonded to 1,3-positions and arachidonic acid is bonded to 2-position. The medium-chain fatty acid is preferably selected from fatty acids having 6 to 12 carbons and, for example, selected from fatty acids having 8 carbons.

The present invention still further provides a food composition where the composition contains not less than 0.001% by weight of a triglyceride in which medium-chain fatty acids are bonded to 1,3-positions and arachidonic acid is bonded to 2-position. The above-mentioned medium-chain fatty acid is preferably selected from fatty acids having 6 to 12 carbons and, for example, selected from fatty acids having 8 carbons. The food composition is, for example, a functional food, a nutritional supplement, a designated health food or a geriatric food.

The present invention still furthermore provides a method for the manufacture of a composition having a normalizing action of infradian rhythm and/or a synchronization promoting action for circadian rhythm (biological clock), characterized in that, arachidonic acid and/or an arachidonic acid-containing compound are/is compounded either solely or together with a food material which contains substantially no arachidonic acid or, even if contained, its amount is small.

Embodiments for Carrying Out the Invention

The present invention relates to a beverage/food having a normalizing action of infradian rhythm and/or a synchronization promoting action for circadian rhythm (biological clock) containing arachidonic acid and/or an arachidonic acid-containing compound, and to a method for producing the same.

The composition of the present invention has a preventive or alleviating action to biorhythm disorder, sleep disorder and delayed sleep phase syndrome caused by abnormality of infradian rhythm and also to disorder caused by retardation of synchronization of circadian rhythm (biological clock) (jet lag, headache, tinnitus, palpitation, nausea, gastralgia, diarrhea and lowering in ability of judgment and concentration) and is effective as beverage/food, health food, functional food, designated health food, food for babies and little children, food and drug for aged people, quasi-drug, etc.

Besides arachidonic acid, it is also possible to utilize any arachidonic acid-containing compound as an effective ingredient of the present invention. Examples of the arachidonic acid-containing compound are salts of arachidonic acid such as calcium salt and sodium salt. Other examples are alcohol esters of arachidonic acid such as methyl arachidonate and ethyl arachidonate. It is further possible to utilize triglyceride, diglyceride, monoglyceride, phospholipid, glycolipid, etc., comprising arachidonic acid as all of or a part of the constituting fatty acid.

When application to food is considered, it is preferred that arachidonic acid is in a form of triglyceride or phospholipid or, particularly preferably, in a form of triglyceride. Although there has been almost no natural source for a triglyceride containing arachidonic acid (which has the same meaning as triglycerides containing a triglyceride comprising arachidonic acid as a part of or all of the constituting fatty acid), it is now possible by the present invention that a triglyceride containing arachidonic acid as a constituting fatty acid is industrially utilized and, as a result of evaluation of an effect on circadian rhythm of rat, the effect of the effective ingredient of the present invention has been clarified and that has been clarified to have a normalizing action for infradian rhythm and/or synchronization promoting action of circadian rhythm (biological clock).

Accordingly, in the present invention, it is possible to use triglycerides containing a triglyceride comprising arachidonic acid as a part of or all of the constituting fatty acid which is an effective ingredient of the present invention (a triglyceride comprising arachidonic acid). With regard to a triglyceride comprising arachidonic acid, fat/oil (triglyceride) where the ratio of arachidonic acid in all fatty acids constituting the triglyceride is not less than 20 weight (w/w) %, preferably not less than 30 weight % or, more preferably, not less than 40 weight % is a preferred form when it is applied to food. Accordingly, in the present invention, any of the products which are prepared by incubation of a microorganism having an ability of production of fat/oil (triglyceride) containing arachidonic acid may be used.

Examples of the microorganism having an ability of production of fat/oil (triglyceride) containing arachidonic acid are those which belong to genus *Mortierella*, genus

*Conidiobolus*, genus *Pythium*, genus *Phytophthora*, genus *Penicillium*, genus *Cladosporium*, genus *Mucor*, genus *Fusarium*, genus *Aspergillus*, genus *Rhodotorula*, genus *Entomophthora*, genus *Echinosporangium* and genus *Saprolegnia*.

With regard to a microorganism belonging to subgenus *Mortierella* in genus *Mortierella*, its examples are *Mortierella elongate, Mortierella exigua, Mortierella hygrophila* and *Mortierella alpine*. To be more specific, strains such as *Mortierella elongate* IFO 8570, *Mortierella exigua* IFO 8571, *Mortierella hygrophila* IFO 5941 and *Mortierella alpine* IFO 8568, ATCC 16266, ATCC 32221, ATCC 42430, CBS 219.35, CBS 224.37, CBS 250.53, CBS 343.66, CBS 527.72, CBS 529.72, CBS 608.70, CBS 754.68, etc. are exemplified.

All of those strains are available from the Institute for Fermentation, Osaka (IFO) in Osaka City, the American Type Culture Collection (ATCC) in U.S.A. and the Central Bureau voor Schimmelcultures (CBS) without any restriction. It is also possible to use *Mortierella elongate* SAM 0219 (Accession No. 8703 deposited at the Fermentation Research Institute) (Accession No. 1239 deposited at the Fermentation Research Institute) which is a strain isolated from a soil by the study group for the present invention.

In the culture of the strain used in the present invention, spores, mycelia or a preculture which was incubated previously are/is inoculated to a liquid medium or solid medium followed by incubating. In the case of a liquid culture, any of commonly used ones as a carbon source such as glucose, fructose, xylose, saccharose, maltose, soluble starch, molasses, glycerol and mannitol may be used although they are non-limitative.

In addition to a natural nitrogen source such as peptone, yeast extract, malt extract, meat extract, Casamino acid, corn steep liquor, soybean protein, defatted soybean and cotton seed cake, it is also possible to use an organic nitrogen source such urea and an inorganic nitrogen source such as sodium nitrate, ammonium nitrate and ammonium nitrate as a nitrogen source. Besides the above, it is further possible to use inorganic salt such as phosphate, magnesium sulfate, iron sulfate and copper sulfate, vitamin, etc. as a minor nutrient if necessary. There is no particular limitation for such components for the culture so far as their concentrations do not deteriorate the growth of the microorganism. Practically and generally, it is recommended that, in the case of carbon source, the concentration is 0.1 to 40 weight (w/v) % or, preferably, 1 to 25 weight (w/v) %. With regard to the initial adding amount of nitrogen source is 0.1 to 10 weight (w/v) % or, preferably, 0.1 to 6 weight (w/v) % and, during the incubation, nitrogen source may be added thereto.

When a carbon source concentration in the medium is controlled, it is also possible to use fat/oil (triglyceride) containing not less than 45 weight (w/w) % of arachidonic acid as an effective ingredient of the present invention. In the incubation, the period from the second to the fourth days is a cell growing period and the period after the second to the fourth day is a fat/oil accumulating period. The initial carbon source concentration is made 1 to 8% by weight or, preferably, 1 to 4% by weight, then a carbon source is successively added during the cell growing period and the fat/oil accumulating period only and the total amount of the successively added carbon source is made 2 to 20% by weight or, preferably, 5 to 15% by weight. Incidentally, the successively added amount of carbon source during the cell growing period and the fat/oil accumulating period is made dependent upon the initial nitrogen source concentration and the carbon source concentration in the medium after the seventh day of the incubation, preferably after the sixth day of the incubation or, more preferably, after the fourth day of the incubation is made 0 whereby a fat/oil (triglyceride) containing not less than 45% by weight of arachidonic acid is able to be prepared and used as an effective ingredient of the present invention.

Temperature for incubation of the arachidonic acid-producing microorganism may vary depending upon the microorganism used and it may be 5 to 40° C. or, preferably, 20 to 30° C. or, after cells are grown by incubating at 20 to 30° C., incubation is continued at 5 to 20° C. whereupon an unsaturated fatty acid is able to be produced. By means of the temperature control as such, it is also possible to raise the ratio of highly-unsaturated fatty acid in the resulting fatty acids. The pH of the medium is made 4 to 10 or, preferably, 5 to 9 and stirring culture with aeration, shake culture or stationary culture is carried out. Incubation is carried out usually for 2 to 30 days, preferably for 5 to 20 days or, more preferably, for 5 to 15 days.

As a further means for increasing the ratio of arachidonic acid in the fat/oil (triglyceride) containing arachidonic acid besides the control of the carbon source concentration in the medium, it is also possible to prepare a fat/oil containing high amount of arachidonic acid by conducting a selective hydrolysis for an arachidonic acid-containing fat/oil. Since lipase which is used for such a selective hydrolysis has no position-specificity for the triglyceride and its hydrolyzing activity lowers in proportion to the numbers of the double bond, an ester bond in the fatty acid which is other than the highly-unsaturated fatty acid is hydrolyzed. Then a transesterification or the like takes place between the resulting PUFA partial glycerides whereupon a triglyceride in which highly-unsaturated fatty acid is enhanced is resulted ("Enhancement of Archidonic: Selective Hydrolysis of a Single-Cell Oil from *Mortierella* with *Candida cylindracea* Lipase": *J. Am. Oil Chem. Soc.*, 72, 1323-1327 (1998)).

As such, the fat/oil (triglyceride) containing a high amount of arachidonic acid which was prepared by a selective hydrolysis of an arachidonic acid-containing fat/oil may be used as an effective ingredient of the present invention. Although the ratio of arachidonic acid to the whole fatty acid in the arachidonic acid-containing fat/oil (triglyceride) of the present invention is preferably high with a purpose of excluding the influence of other fatty acids, there is no limitation to such a high ratio but, actually, there are some cases where the absolute amount of arachidonic acid is important when it is applied to food. Thus, even a fat/oil (triglyceride) containing not less than 10% by weight of arachidonic acid may be substantially used.

In the present invention, with regard to the triglyceride comprising arachidonic acid as all of or a part of the constituting fatty acid, it is also possible to use a triglyceride where medium-chain fatty acids are bonded to 1,3-positions and arachidonic acid is bonded to 2-position. It is further possible to use a fat/oil (triglyceride) containing not less than 5 mol %, preferably not less than 10 mol %, more preferably not less than 20 mol % or, most preferably, not less than 30 mol % of a triglyceride where a medium-chain fatty acids are bonded to 1,3-positions and arachidonic acid is bonded to 2-position. With regard to the medium-chain fatty acid bonding to 1,3-positions of the above triglyceride, that which is selected from fatty acids having 6 to 12 carbons may be used. Examples of the fatty acid having 6 to 12 carbons are caprylic acid and capric acid and a particularly preferred one is 1,3-capryloyl-2-arachidonoyl-glycerol (hereinafter, referred to as "8A8").

The triglyceride where medium-chain fatty acids are bonded to 1,3-positions and arachidonic acid is bonded to 2-position as such is the optimum fat/oil (triglyceride) when babies and aged people are objects. When fat/oil (triglyceride) is ingested and comes into small intestine, it is usually hydrolyzed with pancreatic lipase. That pancreatic lipase is specific to 1,3-positions whereupon 1,3-positions of the triglyceride are cleaved to give two molecules of free fatty acids and, at the same time, one molecule of 2-monoacylglycerol (MG) is produced. The 2-MG has a very high dissolving property for bile acid and has a good absorbability and, therefore, it is said that, usually, fatty acid of 2-position has better absorption.

When 2-MG is dissolved in bile acid, it acts as if it is a surface-active agent enhancing the absorption of free fatty acid. Then the free fatty acid and 2-MG biosynthesize a micelle of a bile acid-complex together with cholesterol, phospholipid, etc., incorporated into epidermal cells of small intestine to re-synthesize triacylglycerol and, finally, released into lymph as chylomicron. However, the fatty acid characteristic of the pancreatic lipase has a characteristic feature that it is high to saturated fatty acid and arachidonic acid is hardly cleaved. Further problem is that, since pancreatic lipase activity is low in babies and aged people, a triglyceride where medium-chain fatty acid is bonded to 1,3-positions and arachidonic acid is bonded to 2-position is the optimum fat/oil (triglyceride).

As one of specific process for the production of a triglyceride where medium-chain fatty acids are bonded to 1,3-positions and arachidonic acid is bonded to 2-position, it is able to be produced by the action of lipase which acts only on ester bonds of 1,3-positions of the triglyceride in the presence of arachidonic acid-containing fat/oil (triglyceride) and medium-chain fatty acid.

The fat/oil (triglyceride) which is used as a starting material is a triglyceride where arachidonic acid is a constituting fatty acid and, when the ratio of arachidonic acid to total fatty acid constituting the triglyceride is high, the temperature is to be set at 30 to 50° C. or, preferably, 40 to 50° C. which is higher than the common enzymatic reaction temperature which is 20 to 30° C. in order to prevent a decrease in the reaction yield as a result of increase in the unreacted fat/oil materials (the starting triglyceride and a triglyceride where only one of fatty acids at 1,3-positions is a medium-chain fatty acid).

Examples of the lipase which specifically acts on the ester bond of 1,3-positions of the triglyceride are that which is produced by microorganism such as genus *Rhizopus*, genus *Rhizomucor* and genus *Aspergillus* and pancreatic lipase of swine. With regard to the lipase as such, commercially available one may be used. Its examples are lipase of *Rhizopus delemar* (Talipase manufactured by Tanabe Seiyaku), lipase of *Rhizomucor miehei* (Ribozyme IM manufactured by Novo Nordisk) and lipase of *Aspergillus niger* (Lipase A manufactured by Amano Seiyaku) although they are non-limitative but anything may be used so far as it is a lipase which is specific to 1,3-positions.

With regard to the form for use of the above lipase, it is desirable to use a lipase immobilized with an immobilizing carrier for making the reaction temperature not lower than 30° C. or, preferably, not lower than 40° C. with a purpose of enhancing the reaction efficiency and with a purpose of adding a heat resistance to the enzyme. With regard to the immobilizing carrier, an ion-exchange resin carrier which is a highly porous resin having pore size of not smaller than about 100 Å such as Dowex Marathon WBA (a trade name; Dow Chemical) may be exemplified.

One part of the immobilizing carrier is suspended in 0.5 to 20 part(s) by weight of an aqueous solution of lipase specific to 1,3-positions and 2 to 5 parts of cold acetone (e.g., −80° C.) to the suspension are added gradually with stirring whereupon a precipitate is formed. An immobilized enzyme is able to be prepared by drying the precipitate in vacuo. In a simple method, 0.05 to 4 part(s) of lipase specific to 1,3-positions to one part of an immobilizing carrier is/are dissolved in a minimum amount of water, the immobilizing carrier is mixed therewith with stirring and the mixture is dried in vacuo to prepare an immobilized enzyme. As a result of the operation as such, about 90% of lipase are fixed on a carrier but the product as it is does not show transesterifying activity at all. Thus, when it is subjected to a pretreatment in a substrate (comprising starting fat/oil and medium-chain fatty acid) to which 1 to 10% (w/v) of water is/are added or, preferably, in a substrate to which 1 to 3% of water is/are added, the immobilized enzyme is able to be most efficiently activated and to be subjected to the manufacture.

In some types of enzymes, amount of water to be added to the present reaction system is very important. Thus, when no water is contained, the transesterifying reaction hardly proceeds while, when the amount of water is much, hydrolysis takes place and recovery rate of the glyceride lowers (when hydrolysis takes place, diglyceride and monoglyceride are produced). However, when an immobilized enzyme which is activated by means of a pretreatment is used in that case, the amount of water to be added to the present reaction system is no longer important and, even in a system containing no water at all, the transesterifying reaction is able to carried out efficiently. It is also possible to omit the pretreatment when the type of the enzyme preparation is duly selected.

When the heat-resistant immobilized enzyme as such is used and enzymatic reaction temperature is raised, it is now possible to efficiently manufacture a triglyceride where medium-chain fatty acid is bonded to 1,3-positions and arachidonic acid is bonded to 2-position without lowering the reactivity even in the case of a fat/oil (triglyceride) containing arachidonic acid having low reactivity to lipase which is specific to 1,3-positions.

In a method for the manufacture of beverage/food having a normalizing action for infradian rhythm and/or a synchronization promoting action for circadian rhythm (biological clock), a compound where arachidonic acid and/or a compound where arachidonic acid is a constituting fatty acid is able be compounded with a material for beverage/food which contains substantially no arachidonic acid or, if contained, its amount is little. Here, the expression that the amount is little means that, even when arachidonic acid is contained in the material for beverage/food and when the food composition compounded therewith is ingested by human being, the amount is still below the ingesting amount of arachidonic acid per day of the present invention which will be mentioned later.

Especially in the case of a triglyceride where a part of or all of the constituting fatty acid is arachidonic acid, there is an unlimited possibility concerning the use of the fat/oil (triglyceride) and that may be used as a material for food, beverage, drug and quasi-drug and an additive thereto. There is no limitation at all for its purpose of use and amount of use.

Besides the general food, examples of the food composition are functional food, nutritional supplement, prepared milk for premature babies, prepared milk for babies, food for babies, food for expectant and nursing mothers and food for aged people. Examples of the food containing fat/oil are natural food which inherently contains fat/oil such as meat, fish and nut; food to which fat/oil is added upon cooking such as soup; food to which fat/oil is added as a heating medium such as doughnut; fat/oil food such as butter; processed food to which fat/oil is added upon processing such as cookie; and food to which fat/oil is sprayed or applied upon finishing the process such as hard biscuit. It is also possible to add to agricultural food, fermented food, livestock food, sea food or beverage which does not contain fat/oil. In addition, the form of functional food, drug and quasi-drug may be acceptable and it may be in a processed form such as enteral nutrient, powder, granule, troche, oral liquid, suspension, emulsion and syrup.

In addition to the effective ingredient of the present invention, the composition of the present invention may contain various carrier and additive which are commonly used for beverage/food, drug or quasi-drug. It is particularly preferred to contain an antioxidant with a purpose of preventing the oxidation of the effective ingredient of the present invention. Examples of the antioxidant are natural ones such as tocopherol compound, flavone derivative, phyllodulcin compound, kojic acid, gallic acid derivative, catechin compound, fukiic acid, gossypol, pyrazine derivative, sesamol, guaiaol, guaiacic acid, p-coumalic acid, nor-dihydroguaiaretic acid, sterol compound, terpene compound, nucleic acid base compound, carotenoid compound and lignan compound and synthetic ones represented by ascorbic palmitate, ascorbic stearate, butylhydroxyanisole (BHA), butylhydroxytoluene (BHT), mono-tert-butylhydroquinone (TBHQ) and 4-hydroxymethyl-2,6-di-tert-butylphenol (HMBP).

Examples of the tocopherol compound are α-tocopherol, β-tocopherol, γ-tocopherol, δ-tocopherol, ε-tocopherol, ξ-tocopherol, η-tocopherol and tocopherol ester (such as tocopherol acetate). Examples of the carotenoid compound are β-carotene, canthaxanthin and astaxanthin.

Besides the effective ingredient of the present invention, the composition of the present invention may contain a carrier such as various carriers, extender, diluent, filler, dispersing agent, excipient, binder solvent (such as water, ethanol and vegetable oil), dissolving aid, buffer, dissolving promoter, gelling agent, suspending agent, wheat flour, rice powder, starch, corn starch, polysaccharide, milk protein, collagen, rice oil and lecithin while examples of additive are vitamin compound, sweetener, organic acid, coloring agent, perfume, moisture preventer, fiber, electrolyte, mineral, nutrient, antioxidant, preservative, aromatic agent, moisturizer and natural food extract and vegetable extract although they are non-limitative.

The main pharmaceutical ingredient of arachidonic acid and a compound where arachidonic acid is a constituting fatty acid is arachidonic acid. It has been reported that ingesting amount of arachidonic acid from food per day is 0.14 g in Kanto District and 0.19 to 0.20 g in Kansai District (*Shishitsu Eiyogaku*, 4, 73-82, 1995) and it is necessary to take the corresponding or more amount of arachidonic acid. Accordingly, the ingesting amount of arachidonic acid and a compound where arachidonic acid is a constituting fatty acid is arachidonic acid according to the present invention for an adult (such as that having a body weight of 60 kg) per day is 0.001 to 20 g, preferably 0.01 to 10 g, more preferably 0.05 to 5 g and, most preferably, 0.1 to 2 g in terms of amount of arachidonic acid.

When the effective ingredient of the present invention is applied to beverage/food, an absolute amount of arachidonic acid to be compounded with food is important as well. However, since the absolute amount to be compounded with beverage/food varies depending upon the ingesting amount of the beverage/food to be compounded, the compounding is conducted so as to make the amount of arachidonic acid not less than 0.0003% by weight, preferably not less than 0.003% by weight or, more preferably, not less than 0.03% by weight when a triglyceride containing a triglyceride where a part of or all of the constituting fatty acid is arachidonic acid is compounded with the food. Further, when a triglyceride where medium-chain fatty acid is bonded to 1,3-positions and arachidonic acid is bonded to 2-position is compounded with food, the amount is not less than 0.001% by weight, preferably not less than 0.01% by weight or, more preferably, not less than 0.1% by weight as a triglyceride where medium-chain fatty acid is bonded to 1,3-positions and arachidonic acid is bonded to 2-position.

When the composition of the present invention is used as a drug, it is manufactured by a method which is common in the field of pharmaceutical preparations such as a method mentioned in the Japanese Pharmacopoeia or a method similar thereto.

When the composition of the present invention is used as a drug, the compounding amount of the effective ingredient in the composition is not particularly limited so far as the object of the present invention is achieved but an appropriate compounding rate may be used.

When the composition of the present invention is used as a drug, it is preferred to administer in a form of unit dosage form and an oral administration is particularly preferred. Dose of the composition of the present invention may vary depending upon age, body weight, symptom, frequency of administration, etc. and it is recommended that, for example, a compound where arachidonic acid and/or a compound where arachidonic acid is a constituting fatty acid according to the present invention is administered per day to an adult (about 60 kg) in an amount of usually about 0.001 to 20 g, preferably about 0.01 to 10 g, more preferably about 0.05 to 5 g or, most preferably, about 0.1 to 2 g in terms of amount of arachidonic acid by dividing into one to three times a day.

Biological clock is present in supraoptic nucleus in the brain. Main fatty acids in phospholipid membrane of the brain are arachidonic acid and docosahexaenoic acid and, when their balance is taken into consideration, a combination of arachidonic acid with docosahexaenoic acid is preferred in the composition of the present invention. Generally, arachidonic acid (an n-6 type unsaturated fatty acid) and docosahexaenoic acid (an n-3 type unsaturated acid) are biosynthesized from linoleic acid and α-linolenic acid, respectively by the same enzyme. Therefore, when arachidonic acid is solely administered, it suppresses the biosynthesis of docosahexaenoic acid. On the other hand, when docosahexaenoic acid is solely administered, it suppresses the biosynthesis of arachidonic acid.

In order to prevent such a disadvantage, it is desirable that arachidonic acid and docosahexaenoic acid are ingested in combination. Since the rate of eicosapentaenoic acid is very low in phospholipid membrane of the brain, it is desirable that eicosapentaenoic acid is rarely contained. A composition which rarely contains eicosapentaenoic acid and contains arachidonic acid and docosahexaenoic acid is more preferred. In a combination of arachidonic acid with docosahexaenoic acid, the ratio (by weight) of arachidonic acid/docosahexaenoic acid is desirably within a range of 0.1 to 15 or, preferably, 0.25 to 10. Beverage/food in which eicosapentaenoic acid in an amount of less than one-fifth (by weight) of arachidonic acid is compounded is most preferred.

EXAMPLES

The present invention will now be more specifically illustrated as hereunder by way of Examples. However the present invention is not limited to the following Examples.

The food composition of the present invention which is beverage/food, health food, functional food, designated health food, food for babies and food for aged people includes the case where it is sold by describing or displaying the following facts on a container for packing the said food composition and/or a tool (such as pamphlet) for promotion of sales of the said food composition. Thus, they are that the said food composition and/or the component in the said food composition have/has a normalizing action for infradian rhythm and/or a synchronization promoting action for circadian rhythm (biological clock) and have/has a preventing or improving action for biorhythm disorder, sleep disorder and delayed sleep phase syndrome caused by abnormality of infradian rhythm and disorder to retardation of synchronization of circadian rhythm (jet lag, headache, tinnitus, palpitation, nausea, gastralgia, diarrhea and lowering in ability of judgment and concentration).

Example 1. Process for the Production of Triglyceride Comprising Arachidonic Acid as a Constituting Fatty Acid

*Mortierella* alpine was used as an arachidonic acid-producing microorganism. A medium (6 kL) containing 1.8% of glucose, 3.1% of defatted soybean powder, 0.1% of soybean oil, 0.3% of $KH_2PO_4$, 0.1% of $Na_2SO_4$, 0.05% of $CaCl_2.2H_2O$ and 0.05% of $MgCl_2.6H_2O$ was prepared in a 10-kL fermentor and the initial pH was adjusted to 6.0. The pre-cultured solution (30 L) was inoculated and subjected to an aeration culture with stirring for 8 days under the condition where temperature was 26° C., aeration was 360 $m^3$/hour and inner pressure was 200 kPa. The agitation rate was adjusted so as to keep the dissolved oxygen concentration 10 to 15 ppm. With regard to glucose concentration, the concentration within a medium was made within a range of 1 to 2.5% until the fourth day by means of flowing-down method and, after that, it was kept at 0.5 to 1% (% hereinabove means weight (w/v) %).

After completion of the culture, cells containing a triglyceride where arachidonic acid is a constituting fatty acid is recovered by filtration and drying and fat/oil was extracted from the resulting cells with hexane and subjected to purifying steps for edible fat/oil (degumming, deacidifying, deodoring and decoloring) to give 150 kg of arachidonic acid-containing triglyceride (where arachidonic acid was bonded to any position of the triglyceride). The resulting fat/oil (triglyceride) was made into a methyl ester and the resulting fatty acid methyl ester was analyzed by a gas chromatography whereupon the ratio of arachidonic acid in the total fatty acid was 40.84%.

Incidentally, palmitic acid, stearic acid, oleic acid, linoleic acid, γ-linolenic acid and dihomo-γ-linolenic acid were 11.63%, 7.45%, 7.73%, 9.14%, 2.23% and 3.27%, respectively. Further, the above arachidonic acid-containing fat/oil (triglyceride) was made into an ethyl ester and a fatty acid ethyl ester mixture containing 40% of ethyl arachidonate was subjected to a conventional high-performance liquid chromatography to separate and purity 99% ethyl arachidonate.

Example 2. Production of Triglyceride Containing not Less than 5% of Triglyceride (8A8) Where Medium-Chain Fatty Acid is Bonded to 1,3-Positions and Arachidonic Acid is Bonded to 2-Position An ion-exchange resin carrier (Dowex Marathon WBA; Dow Chemical; Trade Mark) (100 g) was suspended in 80 ml of a 12.5% aqueous solution of *Rhizopus delemar* lipase (Talipase Powder; Tanabe Seiyaku) and dried in vacuo to give an immobilized lipase.

After that, a reaction was carried out using 80 g of the triglyceride (TGA 40S) containing 40% by weight of arachidonic acid prepared in Example 1, 160 g of caprylic acid, 12 g of the above immobilized lipase and 4.8 ml water at 30° C. for 48 hours with stirring (130 rpm). After completion of the reaction, the reaction solution was removed to give an activated immobilized lipase.

Then the immobilized lipase (*Rhizopus delemar* lipase; carrier: Dowex Marathon WBA, trade mark) (10 g) was filled in a glass column (1.8×12.5 cm; volume: 31.8 ml) equipped with a jacket, a mixed fat/oil where TGA 40S prepared in Example 1 and caprylic acid were mixed in 1:2 was flown into the column at a constant flow rate (4 ml/hour) and a continuous reaction was carried out to give 400 g of a reacted fat/oil. In the meanwhile, temperature of the column was kept at 40 to 41° C. From the resulting reacted fat/oil, unreacted caprylic acid and free fatty acids were removed by means of a molecular distillation followed by subjecting to purifying steps for edible fat/oil (degumming, deacidifying, deodoring and decoloring) to give a fat/oil (triglyceride) containing 8A8.

When the rate of 8A8 in the 8A8-containing fat/oil (triglyceride) prepared by gas chromatography and high-performance liquid chromatography was checked, it was 31.6% (Incidentally, the rates of 8P8, 8O8, 8L8, 8G8 and 8D8 were 0.6, 7.9, 15.1, 5.2 and 4.8%, respectively. Fatty acids P, O, L, G and D bonding to 2-position of the triglyceride were palmitic acid, oleic acid, linoleic acid, γ-linolenic acid and dihomo-γ-linolenic acid, respectively while 8P8 was 1,3-capryloyl-2-palmitoyl-glycerol, 8O8 was 1,3-capryloyl-2-oleoyl-glycerol, 8L8 was 1,3-capryloyl-2-linoleoyl-glycerol, 8G8 was 1,3-capryloyl-2-γ-linolenoyl-glycerol and 8D8 was 1,3-capryloyl-2-dihomo-γ-linolenonyl-glycerol). Incidentally, the resulting 8A8-containing fat/oil (triglyceride) was subjected to a conventional high-performance liquid chromatography to separate and purify 96 mol % of 8A8.

Example 3. Synchronization Promoting Action to Phase Change of Light-and-Dark Cycle of Arachidonic Acid-Containing Fat/Oil Influence of the triglyceride (arachidonic acid-containing fat/oil) where arachidonic acid is a constituting fatty acid prepared in Example 1 on phase change of light-and-dark cycle was investigated in rats.

Rats have a habit that they mostly rest (sleep) in a light period while they are active in a dark period. Therefore, the light-and-dark cycle was changed to an extent of 6 hours before and after that whereby influence to synchronization was checked by means of days until synchronization to new light-and-dark cycle was achieved. Incidentally, to evaluate the synchronization, the infradian rhythm of rats was investigated by measuring the amount of daily movements continuously, and examining changes over time in the amounts of movements in the lights period and the dark period.

Measurement of infradian quantity of motion of rats was carried out in such a manner that the rats were separately raised in a box installed with an infrared sensor and the quantity of motion was counted by the infrared sensor. Thus, whenever the animal passed the infrared sensor, it was taken as one count and the numbers were integrated to give a quantity of motion (counts). Statistic treatment was carried out using ANOVA and Student's t-test.

Twenty male Fischer rats of strain of 18 months age were divided into two groups of a control feed group (10 rats: OC (18M) group) and an arachidonic acid-containing fat/oil-compounded feed group (10 rats: OA (18M) group) and the control feed and the arachidonic acid-containing fat/oil-compounded feed as shown in Table 1 were given after a pre-raising for about two weeks.

TABLE 1

Experimental Feeds

|  | Control Feed | Arachidonic Acid-Containing Fat/Oil-Compounded Feed |
|---|---|---|
| Casein (g/kg) | 200 | 200 |
| DL-Methionine | 3 | 3 |
| Corn Starch | 150 | 150 |
| Sucrose | 500 | 500 |
| Cellulose Powder | 50 | 50 |
| Corn Oil | 50 | 45 |
| Minerals A1N-76 | 35 | 35 |
| Vitamins A1N-76 | 10 | 10 |
| Choline Bitartrate | 2 | 2 |
| Vitamin E | 0.05 | 0.05 |
| Suntga 40 S | 0 | 5 |

Amount of the feed ingested by a rat was about 20 g and a daily ingested amount of arachidonic acid-containing fat/oil per rat was 0.1 g. In the total fatty acid bonding to the arachidonic acid-containing fat/oil prepared in Example 1, arachidonic acid occupied 40% and, therefore, a daily ingested amount of arachidonic acid per rat is 40 mg. The 40 mg correspond to 133 mg/60 kg/day in terms of ingested amount by human being. The animals were raised in an animal house where room temperature was kept at 23.5±1° C. and humidity was kept at 55±5% and the feed and water were taken by the animals freely. A light-and-dark cycle comprised a dark period for 12 hours (01:00 to 13:00) and a light period for 12 hours (13:00 to 01:00).

Infradian quantity of movement was continuously measured as from after 2 weeks since the ingestion of the experimental food (initiation of phase recording). Everyday, total quantity of movement and movement ratio of light phase to the total quantity of movement ([quantity of movement in light period]/[total quantity of movement]×100%) were calculated. On the tenth day from initiation of the phase recording (40th day from initiation of raising; 26th day from the initiation of ingestion of experimental food), the phase of the light-and-dark cycle was made backward for 6 hours (a dark period for 12 hours (07:00 to 19:00) and a light period for 12 hours (19:00 to 07:00)) and days until the circadian rhythm was synchronized were determined. Then, after ten days more (20th day from the initiation of the phase recording), the phase of the light-and-dark cycle was made forward for 6 hours (a dark period for 12 hours (01:00 to 13:00) and a light period for 12 hours (13:00 to 01:00)) and days until the circadian rhythm was synchronized were determined.

The same experiment was carried out in such a manner that eight male rats of Fischer strain of two months age were divided into two groups of a control feel group (4 rats; YC (2M) group) and an arachidonic acid-containing fat/oil-compounded feed group (4 rats; YA (2M) group) and further that eight male rats of Fischer strain of 22 months age were divided into two groups of a control feel group (4 rats; OC (22M) group) and an arachidonic acid-containing fat/oil-compounded feed group (4 rats; OA (22M) group).

There are shown movement ratios (%) of light phase for 12 hours of a control feed group and an arachidonic acid-containing fat/oil-compounded feed group of 2 months age, 18 months age and 22 months age (FIG. 1). It is now apparent that, when an arachidonic acid-containing fat/oil was ingested, the movement ratios (%) of light phase for 12 hours of aged rats (18M and 22M) were significantly suppressed whereby infradian rhythm was optimized.

Then, FIG. 2 shows the days required until synchronization of a control feed group and an arachidonic acid-containing fat/oil-compounded feed group of 2 months age, 18 months age and 22 months age for a backward movement of phase for 6 hours and a forward movement of phase for 6 hours (FIG. 2). With regard to time (days) required for synchronization of circadian rhythm during the phase movement of light-and-dark cycle of the environment, the that in the forward movement of phase was longer than that in the backward movement of phase in the case of young (2M) rats while, in the case of aged (18M and 22M) rats, that in the backward movement of phase was longer than that in the forward movement of phase. However, as a result of ingestion of arachidonic acid-containing fat/oil, time (days) required for synchronization was significantly shortened. Since that was particularly effective in aged rats and change in circadian rhythm upon aging was determined in light synchronization rather than in rhythm dispatch, arachidonic acid was noted to have an action for adjusting the changes upon aging.

Example 4. Synchronization Promoting Action of Arachidonic Acid-Containing Fat/Oil to Backward Movement of Phase and Forward Movement of Phase by Light Stimulation to Rats Under Raising (Free-Run) with a Dark Condition for 24 Hours When a raising was carried out under a dark condition for 24 hours, no information from outside (light) was obtained and, therefore, rats became active in the inherent period (biological clock) (it is called a free-run in such a sense that it is free from synchronization). When the free-run cycle is calculated on the basis of 24 hours and shown in an abscissa being defined as a circadian time, its first half (12 hours) is called a subjective daytime (biological clock judges it as daytime and rats rest) while the second half (12 hours) is called a subjective night (biological clock judges it as night and rats become active). When light is irradiated to rats, the phase of a free-run rhythm moves forward or backward depending upon the period. In Examples, at the circadian time of 15:00, light of 130 luxes was irradiated to check a backward movement of the phase while, at the circadian time of 20:00, the same light was irradiated to check a forward movement of the phase.

Twenty male Fischer rats of strain of 18 months age were divided into two groups of a control feed group (10 rats: OC (18M) group) and an arachidonic acid-containing fat/oil-compounded feed group (10 rats: OA (18M) group) and each group was given with the control feed and the arachidonic acid-containing fat/oil-compounded feed shown in Table 1 after the pre-raising of two weeks as same as in Example 3.

Amount of the feed ingested by a rat was about 20 g and a daily ingested amount of arachidonic acid-containing fat/oil per rat was 0.1 g. In the total fatty acid bonding to the arachidonic acid-containing fat/oil prepared in Example 1, arachidonic acid occupied 40% and, therefore, a daily ingested amount of arachidonic acid per rat is 40 mg. The 40 mg correspond to 133 mg/60 kg/day in terms of ingested amount by human being. The animals were raised in an animal house where room temperature was kept at 23.5±1° C. and humidity was kept at 55±5% and the feed and water were taken by the animals ad libitum. A light-and-dark cycle comprised a dark period for 12 hours (01:00 to 13:00) and a light period for 12 hours (13:00 to 01:00).

As from 70th day after ingestion of the experimental food, a raising under a 24-hour dark condition (free-run) was initiated and the infradian quantity of movement was continuously measured (initiation of phase recording). As from two weeks from the free-run raising, light of 130 luxes was irradiated for 30 minutes at the circadian time of 15:00 as mentioned already and the moved amount of the phase (hours) was measured. Then, after two weeks more, light was similarly irradiated at the circadian time of 20:00 and the moved amount of phase (hours) was measured. The same experiment was carried out by dividing eight male Fischer rats of strain of two months age into a control feed group (4 rats: YC (2M) group) and an arachidonic acid-containing fat/oil-compounded feed group (4 rats: YA (2M) group).

Further, in the case of eight male fats of Fischer strain of 22 months age, they were divided into two groups of a control feed group (4 rats: OC (22M) group) and an arachidonic acid-containing fat/oil-compounded feed group (4 rats: OA (22M) group), raised for 8 days where a light-and-dark cycle comprised a dark period for 12 hours (01:00 to 13:00) and a light period for 12 hours (13:00 to 01:00), then a raising under a 24-hour dark condition (free-run) was initiated at the same time with the initiation of ingestion of the experimental food and an infradian quantity of movement was continuously measured (initiation of phase recording). As from the 12th day since the free-run raising, light of 130 luxes was irradiated for 30 minutes at the circadian time of 15:00 and the moved amount of the phase (hours) was measured. Then, after two weeks more, light was similarly irradiated at the circadian time of 20:00 and the moved amount of phase (hours) was measured.

The result is shown in FIG. 3. Amount of phase movement of circadian rhythm by irradiation of light in the control feed group of 2 months age, 18 months age and 22 months age was not so much affected by age and, as a result of ingestion of arachidonic acid-containing fat/oil, amount of phase movement was increased.

Example 5. Synchronization Promoting Action of 8A8 (96 Mol %) to Phase Change in Light-and-Dark Cycle Influence of 8A8 (96 mol %) prepared in Example 2 on the phase change of light-and-dark cycle was carried out by the same manner as in Example 3.

Twenty male Fischer rats of strain of 18 months age were divided into two groups of a control feed group (10 rats: OC (18M) group) and 8A8-compounded feed group (10 rats: OA (18M) group) and each group was given with the control feed and the 8A8-compounded feed shown in Table 2 after the pre-raising for about two weeks.

TABLE 2

| Experimental Food | | |
|---|---|---|
| | Control Feed | 8A8-Compounded Feed |
| Casein (g/kg) | 200 | 200 |
| DL-Methionine | 3 | 3 |
| Corn Starch | 150 | 150 |
| Sucrose | 500 | 500 |
| Cellulose Powder | 50 | 50 |
| Corn Oil | 50 | 45.8 |
| Minerals A1N-76 | 35 | 35 |
| Vitamins A1N-76 | 10 | 10 |
| Choline Bitartrate | 2 | 2 |
| Vitamin E | 0.05 | 0.05 |
| 8A8 | 0 | 4.2 |

Amount of the feed ingested by a rat was about 20 g and a daily ingested amount of arachidonic acid-containing fat/oil per rat was 0.1 g. Therefore, a daily ingested amount of arachidonic acid per rat is 40 mg. The 40 mg correspond to 133 mg/60 kg/day in terms of ingested amount by human being. The animals were raised in an animal house where room temperature was kept at 23.5±1° C. and humidity was kept at 55±5% and the feed and water were taken by the animals ad libitum. A light-and-dark cycle comprised a dark period for 12 hours (01:00 to 13:00) and a light period for 12 hours (13:00 to 01:00). Infradian quantity of movement was continuously measured as from after 2 weeks since the ingestion of the experimental food (initiation of the phase recording). Everyday, total quantity of movement and movement ratio of light phase to the total quantity of movement ([quantity of movement in light period]/[total quantity of movement]×100%) were calculated.

On the tenth day from initiation of the phase recording (40th day from initiation of raising; 26th day from the initiation of ingestion of experimental food), the phase of the light-and-dark cycle was made backward for 6 hours (a dark period for 12 hours (07:00 to 19:00) and a light period for 12 hours (19:00 to 07:00)) and days until the circadian rhythm was synchronized were determined. Then, after ten days more (20th day from the initiation of the phase recording), the phase of the light-and-dark cycle was made forward for 6 hours (a dark period for 12 hours (01:00 to 13:00) and a light period for 12 hours (13:00 to 01:00)) and days until the circadian rhythm was synchronized were determined. The same experiment was carried out in such a manner that eight male Fischer rats of strain of two months age were divided into two groups of a control feed group (4 rats; YC (2M) group) and 8A8-compounded feed group (4 rats; YA (2M) group).

With regard to the synchronizing days in the backward movement of the phase, the days required for synchronization of the control feed group and the 8A8-compounded feed group of the rats of 2 months age were 3.7 days and 4.1 days, respectively and, in the case of rats of 18 months age, they were 7.28 days and 5.72 days, respectively. With regard to the synchronizing days in the forward movement of the phase, the days required for synchronization of the control feed group and the 8A8-compounded feed group of the rats of 2 months age were 9.8 days and 9.43 days, respectively and, in the case of rats of 18 months age, they were 5.63 days and 3.32 days, respectively. Thus, as a result of ingestion of 8A8, time (days) required for synchronization shortened.

Example 6. Example for Preparation of Capsules Compounded with Fat/Oil (Triglyceride) Comprising Arachidonic Acid as a Constituting Fatty Acid Gelatin (1.00 parts by weight) and 35 parts by weight of glycerol for a food additive were dissolved in water at 50 to 60° C. to prepare a gelatin film having a viscosity of 2,000 cps. Then the arachidonic acid-containing fat/oil (triglyceride) prepared in Example 1 was mixed with 0.05% by weight of vitamin E oil to prepare a content 1. The fat/oil (triglyceride) containing 32 mol % of 8A8 prepared in Example 2 was compounded with 0.05% by weight of vitamin E oil to prepare a content 2.

After that, 50% by weight of arachidonic acid-containing fat/oil (triglyceride) prepared in Example 1 were mixed with 50% by weight of fish oil (tuna oil: rates of eicosapentaenoic acid and docosahexaenoic acid in the total fatty acid are 5.1% and 26.5%, respectively) and then 0.05% by weight of vitamin E oil was mixed therewith to give a content 3. Eighty % by weight of arachidonic acid-containing fat/oil (triglyceride) were mixed with 20% by weight of fish oil (tuna oil: rates of eicosapentaenoic acid and docosahexaenoic acid in the total fatty acid are 5.1% and 26.5%, respectively) and then 0.05% by weight of vitamin E oil was mixed therewith to give a content 4. A 99% ethyl arachidonate prepared in Example 1 was mixed with 0.05% by weight of vitamin E oil to prepare a content 5. Those contents 1 to 5 were used for subjecting to capsule formation and drying by a conventional method to give soft capsules each containing 200 mg of the content.

Example 7. Use for Fat Transfusion

The fat/oil (triglyceride) containing 96% of 8A8 prepared in Example 2 (400 g), 48 g of purified egg yolk lecithin, 20 g of oleic acid, 100 g of glycerol and 40 ml of 0.1N sodium hydroxide were mixed and homogenized and then distilled water for injection was added thereto to make 4 liters. This was emulsified using a high-pressure spraying emulsifier to prepare a lipid emulsion. Each 200 ml of the lipid emulsion was disposed into a bag made of plastic and sterilized with a high-pressure steam at 121° C. for 20 minutes to give a fat transfusion.

Example 8. Use for Juice

β-Cyclodextrin (2 g) was added to 20 ml of a 20% aqueous solution of ethanol, 100 mg of arachidonic acid-containing triglyceride (compounded with 0.05% of vitamin E) prepared in Example 1 were added thereto and the mixture was incubated at 50° C. for 2 hours. After cooling at room temperature (for about 1 hour), incubation was further conducted at 4° C. for 10 hours together with stirring. The resulting precipitate was recovered by centrifugal separation, washed with n-hexane and freeze-dried to give 1.8 g of an inclusion compound of cyclodextrin containing the arachidonic acid-containing triglyceride. The powder (1 g) was homogeneously mixed with 10 liters of juice to prepare a juice which contained the arachidonic acid-containing triglyceride.

The invention claimed is:

1. A method of treating a patient requiring a normalizing action for infradian rhythm and/or a synchronization promoting action for circadian rhythm (biological clock) comprising:
administering a composition containing an arachidonic acid-containing compound to a patient in need thereof in an arachidonic acid amount of 0.1 to 2 g per day, wherein the arachidonic acid-containing compound is an alcohol ester of arachidonic acid or triglyceride or glycolipid comprising arachidonic acid as a part of or all of the constituting fatty acids.

2. The method according to claim 1, wherein the triglyceride comprising arachidonic acid as all of or a part of the constituting fatty acids is a triglyceride where medium-chain fatty acids are bonded to 1,3-positions and arachidonic acid is bonded to 2-position.

3. The method according to claim 2, wherein the medium-chain fatty acid is selected from fatty acids having 6 to 12 carbons.

4. The method according to claim 3, wherein the medium-chain fatty acid is selected from fatty acids having 8 carbons.

5. A method of treating a patient requiring a normalizing action of infradian rhythm and/or a synchronization promoting action for circadian rhythm (biological clock) comprising:
administering a composition containing a triglyceride comprising arachidonic acid as all of or a part of a constituting fatty acids to a patient in need thereof.

6. The method according to claim 5, wherein the ratio of arachidonic acid of the triglycerides containing a triglyceride comprising arachidonic acid as all of or a part of the constituting fatty acids is not less than 10% by weight to total fatty acids which constitute the triglyceride.

7. The method according to claim 5, wherein the triglyceride comprising arachidonic acid as all of or a part of the constituting fatty acids is extracted from a microorganism belonging to genus *Mortierella*.

8. The method according to claim 5, wherein the triglyceride comprising arachidonic acid as all of or a part of the constituting fatty acids is a triglyceride which does not contain eicosapentaenoic acid or, even if contained, its amount is not more than 1%.

9. A method of treating a patient requiring a normalizing action of infradian rhythm and/or a synchronization promoting action for circadian rhythm (biological clock) comprising:
administering a composition containing triglycerides to a patient in need thereof, wherein the triglycerides contain not less than 5 mol % of a triglyceride having a medium-chain fatty acids bonded to 1,3-positions and arachidonic acid bonded to 2-position, and wherein the composition is administered in an arachidonic acid amount of 0.1 to 2 g per day.

10. The method according to claim 9, wherein the medium-chain fatty acid is selected from fatty acids having 6 to 12 carbons.

11. The method according to claim 10, wherein the medium-chain fatty acid is selected from fatty acids having 8 carbons.

12. A method according to claim 1, wherein said administering alleviates in said patient a biorhythm disorder caused by abnormality of infradian rhythm.

13. The method according to claim 12, wherein the composition is administered in an amount effective to alleviate a biorhythm disorder, wherein the biorhythm disorder is a sleep disorder.

14. The method according to claim 12, wherein the composition alleviates a biorhythm disorder caused by retardation of synchronization of circadian rhythm (biological clock).

15. The method according to claim 14, wherein the biorhythm disorder is jet lag, headache, tinnitus, palpitation, nausea, gastralgia, diarrhea or lowering in ability of judgment and concentration.

16. The method according to claim 12, wherein the biorhythm disorder is delayed sleep phase syndrome.

17. The method according to claim 1, wherein the composition is a food composition or a pharmaceutical composition.

18. The method according to claim 17, wherein the arachidonic acid-containing compound is an alcohol ester of arachidonic acid, or triglyceride or glycolipid containing arachidonic acid as a part of or all of the constituting fatty acid.

19. The method according to claim 18, wherein the triglyceride comprising arachidonic acid as all of or a part of the constituting fatty acids is a triglyceride where a medium-chain fatty acids are bonded to 1,3-positions and arachidonic acid is bonded to 2-position.

20. The method according to claim 19, wherein the medium-chain fatty acid is selected from fatty acids having 6 to 12 carbons.

21. The method according to claim 20, wherein the medium-chain fatty acid is selected from fatty acids having 8 carbons.

22. The method according to claim 1, wherein the composition contains not less than 0.001% by weight of a triglyceride in which a medium-chain fatty acid is bonded to 1,3-positions and arachidonic acid is bonded to 2-position.

23. The method according to claim 22, wherein the medium-chain fatty acid is selected from fatty acids having 6 to 12 carbons.

24. The method according to claim 23, wherein the medium-chain fatty acid is selected from fatty acids having 8 carbons.

25. The method according to claim 17, wherein the food composition is a functional food, a nutritional supplement, a designated health food or a geriatric food.

26. A method of treating a patient requiring a normalizing action for infradian rhythm and/or a synchronization promoting action for circadian rhythm (biological clock) comprising:
   administering a composition containing a single active ingredient to a patient in need thereof,
   wherein the single active ingredient consists of an arachidonic acid-containing compound,
   wherein the arachidonic acid-containing compound is an alcohol ester of arachidonic acid or triglyceride or glycolipid comprising arachidonic acid as a part of or all of the constituting fatty acids, and wherein the composition is administered in an arachidonic acid amount of 0.1 to 2 g per day.

* * * * *